(12) United States Patent
Belov et al.

(10) Patent No.: US 7,541,576 B2
(45) Date of Patent: Jun. 2, 2009

(54) METHOD OF MULTIPLEXED ANALYSIS USING ION MOBILITY SPECTROMETER

(75) Inventors: Mikhail E. Belov, Richland, WA (US); Richard D. Smith, Richland, WA (US)

(73) Assignee: Battelle Memorial Istitute, Richland, WA (US)

(*) Notice: Subject to any disclaimer, the term of this patent is extended or adjusted under 35 U.S.C. 154(b) by 290 days.

(21) Appl. No.: 11/701,752

(22) Filed: Feb. 1, 2007

(65) Prior Publication Data
US 2008/0185513 A1  Aug. 7, 2008

(51) Int. Cl.
*H01J 49/40* (2006.01)
(52) U.S. Cl. .......... 250/282; 250/287
(58) Field of Classification Search ......... 250/281, 250/282, 283, 285, 286, 287, 288, 289; 702/23, 702/27
See application file for complete search history.

(56) References Cited

U.S. PATENT DOCUMENTS 5,396,065 A * 3/1995 Myerholtz et al. .......... 250/287
6,300,626 B1 * 10/2001 Brock et al. .............. 250/287
2005/0001163 A1 * 1/2005 Belov et al. .............. 250/290
2006/0054804 A1 * 3/2006 Wexler .................... 250/282

* cited by examiner

*Primary Examiner*—Lisa M Caputo
*Assistant Examiner*—Nicole Ippolito Rausch
(74) *Attorney, Agent, or Firm*—Douglas E. McKinley, Jr.; Allan Tuan

(57) ABSTRACT

A method for analyzing analytes from a sample introduced into a Spectrometer by generating a pseudo random sequence of a modulation bins, organizing each modulation bin as a series of submodulation bins, thereby forming an extended pseudo random sequence of submodulation bins, releasing the analytes in a series of analyte packets into a Spectrometer, thereby generating an unknown original ion signal vector, detecting the analytes at a detector, and characterizing the sample using the plurality of analyte signal subvectors. The method is advantageously applied to an Ion Mobility Spectrometer, and an Ion Mobility Spectrometer interfaced with a Time of Flight Mass Spectrometer.

7 Claims, 9 Drawing Sheets

METHOD OF MULTIPLEXED ANALYSIS USING ION MOBILITY SPECTROMETER

GOVERNMENT RIGHTS

The invention was made with Government support under Contract DE-AC0676RLO 1830, awarded by the U.S. Department of Energy. The Government has certain rights in the invention.

TECHNICAL FIELD

This invention relates to improved methods for analyzing ions. More specifically, this invention relates to improved methods for analyzing ions using an ion mobility spectrometer, either alone or in combination with a time-of-flight mass spectrometer.

BACKGROUND OF THE INVENTION

Since its introduction as an analytical technique in early 1970s, (Karasek, F. W. Anal. Chem., 1974, 46, 710A-717A) ion mobility spectrometry (IMS) has been increasingly applied to the characterization of gas-phase ions in a number of applications, including quality control in semiconductor manufacturing processes, (Carr, T. W. Thin Solid Films, 1977, 45, 115-122) environmental monitoring of air and water, (Eiceman, G. A.; Garcia-Gonzalez, L.; Wang, Y.-F.; Pittman, B. Talanta, 1992, 39, 459-467) detection of explosives, (Lawrence, A. H.; Neudorfl, P. Anal.Chem., 1977, 50, 152-155) and chemical warfare agents and toxins (Kientz, Ch. E. J.Chrom. A, 1998, 814, 1-23, Hill, H. H.; Siems, W. F.; Louis R. H. St.; McMinn, D. G. Anal.Chem., 1990, 62,1201A-1209A). IMS is based on spatial separation of gas-phase ion species due to differences in their mobilities through a buffer gas, analogous to capillary electrophoresis (CE) in the condensed phase.

Coupling of electrospray ionization (ESI) and matrix-assisted laser desorption ionization (MALDI) to IMS has provided an impetus for expanding the realm of IMS capabilities to proteomics and other system biology applications. (Wittmer, D.; Chen, Y. H.; Luckenbill, B. K.; Hill, H. H. Anal. Chem., 1994, 66, 2348-2355, Gillig, K. J.; Ruotolo, B.; Stone, E. G.; Russell, D. H.; Fuhrer, K.; Conin, M.; Schultz, A. J. Anal. Chem., 2000, 72, 3965-3971) The enormous complexity of biological systems, (e.g., >20,000 different proteins may be expressed at detectable levels by a mammalian system (Aebersold, R.; Mann, M. Nature, 2003, 422, 198)) has challenged the separation and analysis power of existing approaches, and to this point has been most effectively addressed by combinations of orthogonal fractionation and separation techniques combined with mass spectrometry (MS) as a final separation stage due to its high sensitivity, resolution, broad dynamic range and accurate mass measurement capability. Protein detection and identification in a variety of important biomedical applications, including discovery of candidate biomarkers in human blood plasma for early cancer detection, represents a significant analytical challenge for condensed phase multidimensional separations coupled to MS, as many proteins of interest are expected at abundance levels far below that of higher abundance proteins. (Anderson, N. L.; Anderson, N. G. Mol. Cell. Proteomics, 2002. 1, 845-867) The large dynamic range of interest ($>10^{10}$), coupled with issues that derive from biological variation, has greatly hindered proteomic approaches for effectively discovering low level candidate biomarkers in such biological fluids. Liquid chromatography (LC)-MS based proteome analysis of human blood plasma has generally involved the coupling of a high abundance protein depletion step with intensive protein and/or peptide level fractionation/separation techniques to obtain a greater analytical "depth of coverage". This approach effectively transforms each sample into many samples, and thus reduces the number of individual samples that can be analyzed. At present, for example, it is not practical to perform in-depth proteomic studies involving several hundred individual human blood plasma samples. This throughput versus proteome analysis coverage tradeoff can be addressed by either increasing the depth of coverage in a single analysis or the throughput of current approaches. Since gas-phase ion separations are typically two to three orders of magnitude faster (~10-100 ms) than fast reversed-phase (RP) LC separations of comparable separation power (~5-10 min), IMS represents an attractive complementary orthogonal separation approach. When introduced between the condensed phase separation and MS analysis, IMS can potentially increase the total effective peak capacity of a fast RPLC-MS platform by over an order of magnitude without affecting the overall analysis speed, and thus help in addressing both the depth of coverage and throughput needs.

IMS, in turn, benefits from coupling with fast MS detection capable of acquiring the entire mass spectrum in a single scan. Young et al. first coupled a lower-pressure IMS to an orthogonal time-of-flight (TOF) analyzer to measure the formation and decomposition rates of hydrates of hydronium ion. (Young, C. E.; Edelson, D.; Falconer, W. E. J. Chem. Phys., 1970, 53, 4295-4302) More recently, this approach was used in combination with ESI for characterization of different biochemical compounds. (Guevremont, R.; Siu, K. W. M.; Wang, J.; Ding, L. Anal. Chem., 1997, 69, 3959-3965, Hoaglund, C. S.; Valentine, S. J.; Counterman, A. E.; Clemmer, D. E. Anal. Chem., 1998, 70, 2236-2242) Despite its attractiveness for higher throughput proteomic studies, the application of IMS-MS has been limited by low sensitivity primarily arising from ion losses at the IMS-MS interface and low duty cycle. Tang et al. have recently reported on ion lossless IMS-MS separations with an IMS drift tube incorporated between two electrodynamic ion funnels. (Tang, K.; Shvartsburg, A. A.; Lee, H.-N.; Prior, D. C.; Buschbach, M. A.; Li, F.; Tolmachev, A. V.; Anderson, G. A.; Smith, R. D. Anal. Chem., 2005, 77, 3330-3339) In that experiment, ions were trapped in an "hourglass" ion funnel for 50 to 100 ms at an elevated pressure of 4 Torr and then gated into the IMS drift tube in short 50 μs pulses. At the exit of the IMS drift tube, ion packets, spatially dispersed mainly due to thermal diffusion, were captured by a regular ion funnel followed by a short collisional quadrupole. (Spangler, C. E.; Colins, C. L. Anal. Chem., 1975, 47, 403-407) These developments have also recently been adopted by Clemmer and coworkers. (Koeniger, S. L., Merenbloom, S. I., Valentine, S. J, Jarrold, M. F., Udseth H. R., Smith, R. D., Clemmer, D. E. Anal. Chem., 2006, 78, 4161-4174) Though ion transmission drastically improved as compared to earlier implementations of IMS-oTOF design, lower efficiency of ion trapping/accumulation in the ion funnel still limits the ion utilization efficiency or duty cycle. (Hoaglund-Hyzer, C. S.; Clemmer, D. E. Anal. Chem., 2001, 73, 177-184).

The duty cycle of IMS with a continuous ion source can be improved using a Fourier transform (FT) approach. (Knorr, F. J.; Eatherton, R. L.; Siems, W. F.; Hill, H. H., Jr. Anal. Chem., 1985, 57, 402-406; St. Louis, R. H.; Siems, W. F.; Hill, H. H. Anal. Chem., 1992, 64, 171-177) Using two gates at the entrance and at the exit of the drift region allows the "front" and "exit" gate opening and closing voltages to be correlated with the drift time for ions of interest. This approach provided a 3- to 5-fold increase in the signal-to-noise ratio (SNR) for the ions of a specific drift time at any given moment. Obtaining improved sensitivity for all species in a single IMS separation, requires a multiplexing technique, such as the Hadamard transform (HT). HT has been extensively used in optical spectrometry for over five decades. (Harwit, M.; Sloane, N. J. *Hadamard Transform Optics*; Academic Press: New York, 1979) The concept of measuring different bundles of objects by weighing them in groups rather than individually was first proposed by Fellgett, and the resulting increase in accuracy is sometimes called the Felgett or multiplex advantage. (Felgett, P. *The theory of infrared sensitivities and its application to investigations of stellar radiation in the near infrared*, PhD thesis, Cambridge University; Fellgett, P. J. de Physique, 1967, 28, 165-171) If spectral line intensities are simultaneously detected in N measurements, the theoretical increase in SNR over a single measurement is then expected to be ~$\sqrt{N}$. Decker has experimentally demonstrated such an SNR gain by comparing the mercury vapor emission spectra obtained with both a monochromator and a Hadamard transform spectrometer. (Decker, J. A. *Appl. Opt.*, 1971, 10, 510-514) HT has been successfully applied to TOF MS and capillary electrophoresis (CE), yielding an increase in the duty cycle up to 50%. In CE experiments with fluorescence detection, Kaneta et al have experimentally demonstrated an SNR increase by a factor of 8, which was in excellent agreement with the theoretically predicated value of 8.02. (Kaneta, T.; Yamaguchi, Y.; Imasaka, T. *Anal.Chem.*, 1999, 71, 5444-5446) CE multiplexing was achieved by photodegradation of a light-absorbing analyte, an approach that would be difficult to implement with a complex biological sample. For an HT on-axis TOF MS a proof-of-principle has been demonstrated using both direct infusion and CE, although no comparison with conventional signal averaging was reported. (Brock, A.; Rodriguez, N.; Zare, R. N. *Anal. Chem.*, 1998, 70, 3735-3741; Fernandez, F. M.; Vadillo, J. M.; Kimmel, J. R.; Weterhall, M.; Markides, K.; Rodriguez, N.; Zare, R. N. *Anal. Chem.*, 2002, 74, 1611-1617). A 5- to 6-fold increase in sensitivity has recently been reported in HT measurements using atmospheric-pressure IMS separations (without MS). (Clowers, B. H.; Siems, W. F.; Hill, H. H.; Massick, S. M. *Anal.Chem.*, 2006, 78, 44-51; Szumlas, A. W.; Ray, S. J.; Hieftje, G. M. *Anal. Chem.*, 2006, 78, 474-4471) This improvement, however, falls short of the theoretically expected gain of 15 to 45 (the theoretical gain for a 13-bit sequence is $$\frac{\sqrt{2^{13}-1}}{2} \cong 45.25 \Big).$$

The discrepancy can be explained, in part, by the fact that the encoding pseudo-random binary sequence used in these multiplexing experiments exceeded the ion mobility drift times by almost two orders of magnitude. As a result, only a small fraction of the sequence contributed to any SNR enhancement as compared to that of a conventional averaging approach.

In sum, a major potential attraction of the IMS-TOF MS platform is separation speeds exceeding that of conventional condensed phase separations by orders of magnitude. Known limitations of the IMS-TOF MS platforms that presently mitigate this attraction include the need for extensive signal averaging due to factors that include significant ion losses in the IMS-TOF interface and an ion utilization efficiency of less than ~1% with continuous ion sources (e.g., ESI). Accordingly, there exists a need for improved methods of analyzing ions using an Ion Mobility Spectrometer, and there exists a further need for improved methods of analyzing ions in arrangements where an Ion Mobility Spectrometer is interfaced with a Time of Flight Mass Spectrometer.

SUMMARY OF THE INVENTION

One object of this invention is to provide an improved method for analyzing analytes using a Spectrometer, and preferably, analyzing ions using an Ion Mobility Spectrometer.

A second object of this invention is to provide an improved method for analyzing ions in arrangements where an Ion Mobility Spectrometer is interfaced with a Time of Flight Mass Spectrometer.

These and other objects of the present invention are achieved by providing a method for analyzing analytes from a sample introduced into an spectrometer. Spectrometers that may take advantage of the present invention include, but are not limited to, ion mobility spectrometers, capillary electrophoresis spectrometers, mass spectrometers, liquid chromatographs, and the like. As is typical in the operation of spectrometers, the present invention begins with the step of introducing analytes into the spectrometer. In the present invention, this is accomplished with a gate that is either open, allowing analyte into the spectrometer, or closed, thereby preventing analyte from entering the spectrometer.

For example, in the case of an ion mobility spectrometers, the present invention is a method for analyzing an ion beam from a sample introduced into an ion mobility spectrometer. As is typical in the operation of ion mobility spectrometers, the present invention begins with the step of accumulating ions in an ion trap having a gate from the sample provided to the ion mobility spectrum as an ion beam. The present invention then generates a pseudo random sequence of a modulation bins.

As used herein, a "modulation bin" simply refers to a defined segment of time. While not meant to be limiting, a modulation bin may be coded in a vector. For example, and also not meant to be limiting, the pseudorandom series of modulation bins of the present invention may be coded as a series of ones and zeros in a vector, where a one represents a modulation bin (or period of time) that contained a gate open event, and a zero represents a modulation bin (or period of time) that did not contain a gate open event. A "gate open event" in the context of an ion mobility spectrometer is simply a period of time that the gate of the ion trap is open, thereby allowing ions accumulated in the trap to pass further into the ion mobility spectrometer, and a "gate closed event" in the context of an ion mobility spectrometer is simply a period of time that the gate of the ion trap is closed, thereby allowing ions to accumulate in the trap.

As will be recognized by those having ordinary skill in the art, it is not necessary to have a trap, or to accumulate ions in the trap, of an ion mobility spectrometer. Further, other spectrometers are operated without traps. Thus, in those contexts, a gate open event, simply means an event where anlayte is being introduced into the spectrometer, and a gate closed event, simply means an event where anlayte is not being introduced into the spectrometer.

According to the example, a vector representing a pseudo-random sequence of modulation bins would thus consist of a series of ones and zeros in a pseudorandom sequence in which a "1" corresponded to the periods of time during which the gate to the ion trap was opened, and a "0" corresponded to periods of time during which the gate to the ion trap remained closed. It is important to note that modulation bin represented by a "1" would not correspond to the entire period of time during which the gate to the ion trap was open, but rather to a period of time which included a smaller period of time during which the gate to the ion trap was opened. Thus, a modulation bin represented by a "1" would include both a period of time during which the gate to the ion trap was open, and also a period of time during which the gate to the ion trap was closed.

As used herein, a "pseudorandom sequence" is a sequence that appears random but is not. Typically, pseudorandom sequences exhibit statistical randomness but are generated by an entirely deterministic causal processes, such that that they are easier to produce than a genuine random sequences, and have the benefit that they can be used again and again to produce exactly the same sequences.

The present invention organizes each modulation bin as a series of submodulation bins, thereby forming an extended pseudo random sequence of submodulation bins. As with modulation bins, submodulation bins are also simply defined segments of time. Specifically, a submodulation bin is simply a segment of time included in a longer segment of time that comprises a modulation bin.

The submodulation bins are of equal duration, and each submodulation bin is itself either a gate open event, or a gate closed event. Accordingly, each gate open event and each gate closed event may also be represented by as a series of ones and zeros in a vector, where a one represents a submodulation bin that was a gate open event, and a zero represents a submodulation bin that was a gate closed event. Each modulation bin thus consists of a series of submodulation bins. Each modulation bin is either a gate open event followed by a series of gate closed events, or a series of gate closed events.

Thus, by way of example, and not meant to be limiting, a pseudorandom sequence of modulation bins may consist of the vector 10010. If each modulation bin consists of ten submodulation bins, then the extended pseudorandom sequence of the submodulation bins that make up this exemplary modulation bin would consist of a vector representing 50 submodulation bins. The first group of ten of these submodulation bins would correspond to a modulation bin coded as a 1, and therefore would represent a gate open event followed by nine gate closed events, or a vector of submodulation bins that could be coded as 1000000000. The second group of ten of these submodulation bins would correspond to a modulation bin coded as a 0, and therefore would represent ten consecutive gate closed events, or a vector of submodulation bins that could be coded as 0000000000. The third group of ten of these submodulation bins would also correspond to a modulation bin coded as a 0, and therefore would again represent ten consecutive gate closed events, or a vector of submodulation bins that could be coded as 0000000000. The fourth group of ten of these submodulation bins would correspond to a modulation bin coded as a 1, and therefore would represent a gate open event followed by nine gate closed events, or a vector of submodulation bins that could be coded as 1000000000. Finally, the fifth group of ten of these submodulation bins would correspond to a modulation bin coded as a 0, and therefore would represent ten consecutive gate closed events, or a vector of submodulation bins that could be coded as 0000000000.

The extended pseudo random sequence of these submodulation bins would thus consist of the combined vector of all of these submodulation bins, corresponding to the five modulation bins, 10010. The vector of the extended pseudo random sequence of these submodulation bins would thus be 10000000000000000000000000000001000000000000000000.

The present invention includes the step of releasing the ions in a series of ion packets with a series of gate open events according to the pseudo random sequence of modulation bins, wherein each ion packet consists of ions released by a given gate open event, thereby generating an unknown original ion signal vector. The accumulated ions of each ion packet released from the ion trap are then accelerated through the ion mobility spectrometer; and then detected at a detector, wherein ions of sequential packets are intermingled at the detector, thereby generating a plurality of ion signal subvectors equal to the number of submodulation bins. Using this information, the present invention is able to characterize the sample of ions with a signal to noise ratio heretofore unknown in prior art methods, with no degradation of resolution. Accordingly, the present invention includes the step of characterizing the sample using the plurality of ion signal subvectors.

Not meant to be limiting, the step of characterizing the sample using the plurality of ion signal subvectors preferably is accomplished by first folding the extended pseudo random sequence of submodulation bins to produce weighed pseudo random sequence, wherein the weights account for the accumulation time before each gate open event. Then, a weighed matrix is generated from the weighed sequence using a shift register technique. An inverse of the weighed matrix is then generated. Finally, the unknown original ion signal vector is reconstructed by multiplying the inverse matrix by each of the ion signal subvectors, and organizing the products into a vector.

Another aspect of the method of the present invention may also be advantageously practiced using an Ion Mobility Spectrometer interfaced with a Time of Flight Mass Spectrometer to analyze an ion beam from a sample. In this embodiment, ions are again accumulated from the sample in an ion trap having a gate. A pseudo random sequence of a modulation bins is again generated, and each modulation bin is again organized as a series of submodulation bins. An extended pseudo random sequence of submodulation bins is again formed, wherein each submodulation bin is either a gate open event or a gate closed event, the submodulation bins are of equal duration, and each modulation bin consists of either a gate open event followed by a series of gate closed events, or consists of a series of gate closed events. Ions are again released in a series of ion packets with a series of gate open events according to the pseudo random sequence of modulation bins, wherein each ion packet consists of ions released by a given gate open event, thereby generating an unknown original ion signal vector.

In this embodiment, accumulated ions of each ion packet released from the ion trap are accelerated through the Ion Mobility Spectrometer, thereby intermingling the ions from successive ion packets. Ion packets from the Ion Mobility Spectrometer are then accelerated through a time of flight mass spectrometer. Accelerated ions from the time of flight mass spectrometer are then detected at a detector in a series of time of flight bins. As with modulation bins and submodulation bins, time of flight bins are simply units of time. In this case, the length of time of flight bins are typically determined by the data acquisition software and associated circuitry that operates the detector used in the time of flight mass spectrometer. As ions of sequential packets are intermingled at the detector, the data generated by these ions interacting with the detector is organized into a series of time of flight bins. In this manner, a plurality of ion signal subvectors equal to the number of time of flight bins in each submodulation bin is generated. The sample is then characterized using the plurality of ion signal subvectors.

While not meant to be limiting, in an embodiment of the present invention where an Ion Mobility Spectrometer is interfaced with a Time of Flight Mass Spectrometer, the step of characterizing the sample is preferably performed by folding the extended pseudo random sequence of submodulation bins to produce weighed pseudo random sequence, wherein the weights account for the accumulation time before each gate open event. A weighed matrix is then generated from the weighed sequence using a shift register technique. An inverse weighed matrix is then generated from the weighed matrix. Finally, the unknown original ion signal vector is reconscructed by multiplying the inverse matrix by each of the ion signal subvectors and organizing the products into a vector.

In both embodiments of the present invention, using an ion mobility spectrometer, and using an Ion Mobility Spectrometer interfaced with a Time of Flight Mass Spectrometer, it is preferred that the accumulating, accelerating, and detecting steps be repeated for a plurality of sequences, wherein the accelerated ions travel along a flight path such that flight times of the ions to the detector vary with characteristics of the ions, and wherein the characterizing step comprises recovering a mass spectrum of at least one sequence from the intermingled ions. In this manner, each sequence may define a scan, and the characterizing step may further sum a plurality of scans.

For the purposes of promoting an understanding of the principles of the invention, reference will now be made to the embodiments illustrated in the drawings, and certain experiments conducted with these embodiments to demonstrate the present invention. Specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

DETAILED DESCRIPTION OF THE PREFERRED EMBODIMENTS

A series of experiments were conducted to illustrate the operation of a preferred embodiment of the present invention.

Figure 1:
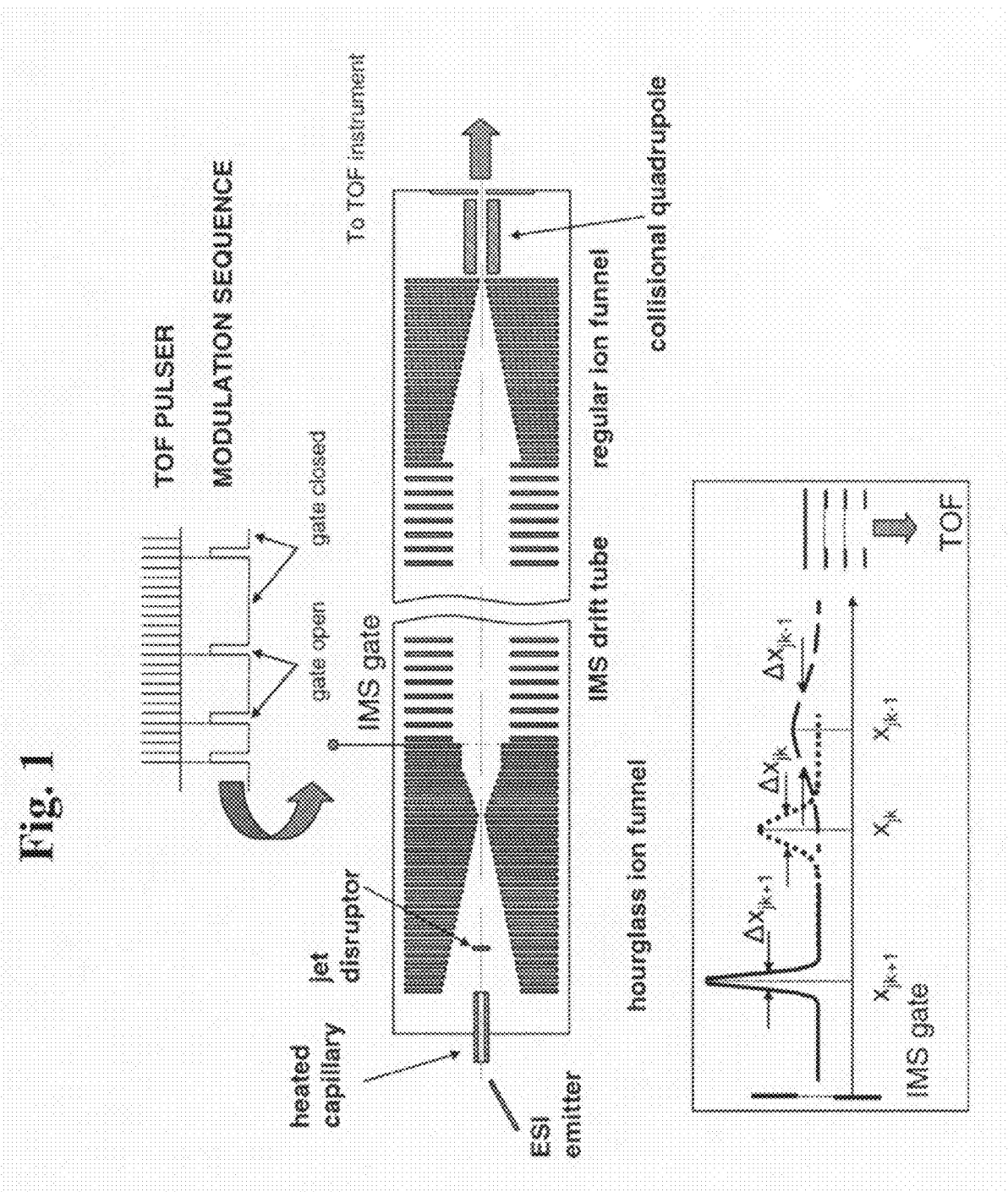
FIG. 1. is a schematic of the ESI multiplexed IMS-TOF MS instrumentation used in experiments which demonstrated a preferred embodiment of the present invention. The IMS gate shown in the Figure is modulated using a pseudo-random binary sequence. Gate open events are synchronized with TOF extraction pulses, resulting in <1 ns timing jitter. The inset schematically shows ion dispersion in the IMS instrument. Indexes k and j correspond to the modulation bin number and the elapsed time, respectively.

The multiplexed IMS-TOF MS approach of the present invention has been implemented using two commercial orthogonal TOF instruments; a Q-Star Pulsar (Sciex, Toronto, Canada) and an Agilent TOF (Agilent, Santa Clara, Calif.) arranged as shown in FIG. 1. The design of the ESI source and IMS drift tube coupled to both TOF spectrometers was as described in Tang, K.; Shvartsburg, A. A.; Lee, H.-N.; Prior, D. C.; Buschbach, M. A.; Li, F.; Tolmachev, A. V.; Anderson, G. A.; Smith, R. D. Anal. Chem., 2005, 77, 3330-3339. The ESI source incorporated a 50-um-i.d. fused silica tip electrospraying into a 64 mm-long 430-um i.d. heated inlet capillary operating at a temperature of ~120° C. The ESI emitter was mounted on a 2D translation stage enabling fine position adjustment with respect to the inlet. All voltages in the ESI source were referenced to a 4 kV potential applied to the IMS drift tube.

Following droplet desolvation in the inlet capillary, intact ions were introduced into an "hourglass" ion funnel at 4 Torr for further trapping and accumulation. The hourglass ion funnel consisted of 0.5 mm-thick 100 ring electrodes, separated by 0.5 mm-thick Teflon spacers. The front section of the funnel incorporated a tapered converging assembly of 42 electrodes whose diameter was linearly decreasing from 25.4 mm to 2 mm. The exit diverging section of the hourglass ion funnel encompassed a set of 10 electrodes of 25.4-mm in diameter (20-mm in diameter for the funnel coupled to Agilent TOF), with a 20 lines/inch mesh (Buckbee-Mears, St. Paul, Minn.) mounted on the exit funnel plate. The first and the last-but-one electrodes of the straight exit section of ion funnel were independently driven at a potential of 40 V, while the potential at the exit electrode was switched between 60 V and 28 V, enabling ion accumulation and gating into the IMS drift tube, respectively. Ion packet multiplexing was conducted by encoding the gating potential (i.e., a potential applied to the funnel exit electrode) with a pseudo-random binary sequence (PRS). Switching potentials on the ion funnel floating at 4 kV potential was implemented with a fiber-optic triggering circuitry. Similar to the conventional ion funnel shown in Belov, M. E.; Gorshkov M. V.; Udseth, H. R.; Anderson, G. A.; Smith R. D. Anal.Chem., 2000, 72, 2271-2279, an alternating rf potential at a frequency of 500 kHz and a peak-to-peak amplitude of 90 V was applied to all funnel plates except for the last dc-only, plate, and a dc gradient of 24 V/cm was produced to assist ion transmission in the axial direction.

An IMS drift tube, coupled to the TOF Q-Star Pulsar, consisted of 55-mm-i.d. 80-mm o.d. 210 copper electrodes separated by 10 mm-long tubular plastic spacers, establishing a 2100-mm-long separation region. Pressure in the drift region was ~4 Torr ($N_2$) and the electric field strength was ~2 kV/m. An 840-mm long IMS drift tube interfaced to Agilent TOF was operated under 2.8 Torr pressure ($N_2$) and electric field strength identical to that used in the IMS-Q-Star instrument.

To capture all ions exiting the IMS separation region, an additional 100-mm-long ion funnel was employed. This funnel was driven at the same rf and dc fields as the front-end hourglass funnel, and then coupled to a 25 mm-long collisional quadrupole operating at a frequency of 2 MHz and a peak-to-peak amplitude of 200 V. The quadrupole manifold was evacuated by a mechanical pump (Alcatel 2033, 12.8 L/s) to provide a pressure drop to ~140 mTorr and an interface for the IMS drift region to the lower-pressure rf ion guides of the commercial TOF instruments.

Both the Q-Star Pulsar and Agilent TOF were coupled to a 10 GHz time-to-digital converter, TDC (Ortec 9353, Oak Ridge, Tenn.). Timing sequences were set by an I/O control board PCI-6711 (National Instruments, Austin, Tex.) installed in a Dell PC running on Windows XP operating system. Data acquisition software was developed in-house using Visual C# and implemented on top of the Active X controls running Ortec hardware. The data acquisition software is available through the United States Department of Energy's Pacific Northwest National Laboratory. To synchronize IMS and MS operations, the IMS pulsing period was made divisible by the TOF acquisition period and user-defined from the data acquisition software. Once the desired sequence for multiplexing was programmatically generated, the PRS was uploaded to PCI-6711 that was triggered by a TOF extraction pulse. In this approach, an electronic jitter of <1 ns was achieved between the onset of TOF spectrum acquisition and triggering signal employed for opening or closing an IMS gate. The IMS gate opening time in both standard and multiplexed experiments was 100 µs. A typical IMS separation and TOF scan durations were 127 ms and 100 µs, respectively. Each TOF mass spectrum acquisition was digitized at 1.6 ns resolution (i.e., 2N×0.1 ns, where N=4), yielding 62,500 TOF bins per TOF scan and ~8×10$^9$ bins per single IMS separation.

Peptides used in this study were purchased from Sigma Aldrich (St. Louis, Mo.) and further analyzed without additional purification. Samples diluted in water:methanol:acetic acid buffer (79.64:20:0.36 v %) were introduced into the instrument at a flow rate of 0.4 µL/min by a syringe pump (KD Scientific, Holliston, Mass.).

These experiments extensively modeled the reconstruction of signals generated in the multiplexed IMS-TOF MS approach using Microsoft Visual C++. Modeling was performed by assuming that i) ion packet broadening in the IMS drift tube is mainly driven by thermal diffusion, facilitating independent ion packet dispersion, and ii) the spatial distribution of an ion cloud is governed by the central limit theorem, resulting in a Gaussian ion density profile along the IMS drift axis. Although space charge effects contribute to the overall expansion of an ion cloud in the IMS drift tube, (as described in Spangler, G. E. Anal. Chem., 1992, 64, 1312) the estimations indicated they contributed <5% of that exerted by the thermal diffusion under our experimental conditions, which account for ~1 nA pulsed ion current resulting from ion accumulation in the funnel.

Ion motion in the IMS drift tube is determined by the ion mobility constant, K, whose equation was derived by Revercomb and Mason in Revercomb, H. E.; Mason, E. A. Anal.Chem., 1975, 47, 970-983:

$$K = \frac{3}{16} \frac{Ze}{N} \sqrt{\frac{2\pi}{kT}\left(\frac{1}{m} + \frac{1}{M}\right)} \frac{1}{\Omega_0} \qquad (1)$$

where Ze is the ion charge, N is the number density of the gas, m and M are the masses of the drift gas and analyte, respectively, k is Boltzmann's constant, T is the absolute temperature of the drift gas, and $\Omega_0$ is the diffusion collision integral. The drift velocity, $v_d$, in the lower electric field of intensity E is determined by the field-independent ion mobility constant, K, as follows:

$$v_d = KE \quad (2)$$

Identical ion species whose gating into the IMS drift tube is determined by a PRS were considered first. Since ion packets disperse along the drift axis independently of each other, the temporal, $\Delta t_{j,k}$, and spatial spread, $\Delta x_{j,k}$, of an ion packet within the IMS drift tube can be estimated as:

$$\Delta t_{j,k} = \sqrt{t_g^2 + \left(\frac{t_{j,k}}{R_d}\right)^2} \quad (3)$$

$$\Delta x_{j,k} = v_d \Delta t_{j,k} \quad (4)$$

$$t_{j,k} = \text{t\_TOF} \times j - \text{t\_offset}_k \quad (5)$$

$$\text{t\_offset}_k = \text{t\_TOF} \times k \times PRS_k \quad (6)$$

$$R_d = \sqrt{\frac{ZeEL_d}{kT\ln 2}} \quad (7)$$

$$x_{j,k} = v_d t_{j,k} \quad (8)$$

where j is the temporal step index, k is the modulation bin index within PRS, $PRS_k$ is the digital '1' or '0' event, which represents an "on" or "off" gate status, t_TOF x j is the elapsed time synchronized with the PRS onset, $\text{t\_offset}_k$ is the temporal offset of the ion packet gated into the IMS drift tube in k-th modulation bin relative to the PRS onset, $t_{j,k}$ is the drift time of the ion packet gated into the IMS drift tube in k-th modulation bin, $t_g$ is the gate opening time, t_TOF is the spectrum acquisition rate with a TOF mass spectrometer, $x_{j,k}$ position of the center of kth ion packet at time $t_j$, $R_d$ is the diffusion-only resolving power as described in Revercomb, H. E.; Mason, E. A. *Anal.Chem.*, 1975, 47, 970-983 and $L_d$ is the length of the IMS drift tube. In multiplexing approach, ion packet gating into the IMS drift tube occurs at different times during the IMS separation, and gating events are delayed relative to the PRS onset. Equations 3, 4, 5, and 8 determine the temporal spread, spatial spread, drift time and drift distance of an ion packet gated into the IMS drift tube in k-th modulation bin, respectively. Index j indicates that the measurements of the above metrics are performed at a time instant of t_TOF x j. Index k corresponds to the modulation bin number and accounts for the delay between the PRS onset and gating event (Equation 6). Equation 3 is similar to that reported previously in Revercomb, H. E.; Mason, E. A. *Anal- .Chem.*, 1975, 47, 970-983 and Asbury, G. R.; Hill, H. H. J. *Microcolumn Separations*, 2000, 12, 172-178, except for the dependence of the drift time on the modulation bin number, a difference that can be better understood by examining a snapshot of IMS separation at the end of the encoding sequence. In this case, an ion packet launched into the IMS drift tube by the first "gate on" event would approach the end of the drift region and exhibit the full dispersion due to thermal diffusion, while the temporal spread of an ion packet gated into the drift region just before taking the snapshot would be characterized only by the gate opening time, $t_g$. At a given elapsed time, the spatial distribution of ions within different ion packets would depend on ion packet position along the drift tube. The inset in FIG. 1 schematically shows ion packet dispersion in the IMS drift tube. For the three ion packets illustrated, the area under the curve is conserved, representing the number of ions injected into the IMS instrument during constant gate opening intervals, while the positions of the maxima and the spatial distributions are determined by Equations 3-8.

The number of ions as a function of their position along the IMS drift tube can be then evaluated as $$\text{N\_ions\_IMS}_{i,j,k} = \frac{N_{i+1,j,k} - N_{i,j,k}}{2} \quad (9)$$

$$N_{i,j,k} = N_0 \int_{x_{j,k}-\text{step}\times i}^{x_{j,k}+\text{step}\times i} \frac{1}{\sqrt{2\pi}\,\Delta x_{j,k}} \exp\left(\frac{-(x - x_{j,k})^2}{2\left(\frac{\Delta x_{j,k}}{2}\right)^2}\right) dx \quad (10)$$

where i is the spatial step index, step is the spatial step, $N_0$ is the total number of ions in a given packet, $N_{i,j,k}$ the number of ions within a spatial interval of $\lfloor x_{j,k}-\text{step}\times i; x_{j,k}+\text{step}\times i \rfloor$, and $\text{N\_ions\_IMS}_{i,j,k}$ is the number of ions within a spatial interval of $\lfloor x_{j,k}+\text{step}\times i; x_{j,k}+\text{step}\times(i+1) \rfloor$ along the IMS drift tube. Note, that $N_0$ is considered to be a time-independent constant that is a first-order approximation for a relatively stable continuous ion source, such as from ESI. A three-dimensional integral, $\text{N\_ions\_IMS}_{i,j,k}$, interpolated with Chebyshev's polynomials in the software, defined the spatial distribution of all ion packets along the IMS drift axis at any given time.

To convert the spatial distribution of ions in the IMS drift tube to the number of ions to be extracted into the orthogonal TOF MS flight tube, ion signals from all the ion packets in the IMS drift tube that contribute to the ion distribution inside the TOF extraction region were summed for each TOF mass spectrum acquisition. Importantly, since the PRS is synchronized with a TOF pulser (see Equations 5-6), each summation corresponded to the number of ions that were gated into the TOF flight tube. Modeling also allowed for the over-sampling of the modulation bins, so that a modulation bin width could be a multiple of several TOF acquisitions. Given an ion's mass-to-charge ratio, $(m/z)_n$ and a calibration coefficient, slope, a TOF function, $TOF_n$ $$TOF_n = \frac{\sqrt{\left(\frac{m}{z}\right)_n}}{\text{slope}} \quad (11)$$

was then added to the total IMS drift time and the ion arrival time at the detector was obtained.

Typical parameters used for ion mobility modeling included an IMS drift tube length of 2 m, an IMS drift tube pressure of 4 Torr, and an electric field strength in the IMS drift region of 2 kV/m, corresponding to 4 kV potential applied to the first IMS electrode. TOF parameters in the reflectron mode were chosen such that m/z 500 would arrive at the TOF detector in 50 us following the extraction pulse. The length of the TOF extraction region (where signals from all ion packets encoded by the PRS were summed) was 30 mm. The encoding 9-bit sequence comprised 511 modulation bins that were each 200 us-long, giving rise to an IMS separation time of ~100 ms. Each modulation bin was synchronized with a 100 us-long TOF mass spectrum acquisition, that, in turn, incorporated $10^3$ TOF detector bins. The TOF detector bin width of 100 ns was limited only by a PC SDRAM, and was considered to be adequate for multiplexed IMS-TOF modeling. Given the TOF acquisition rate, signal reconstruction was performed at an over-sampling rate of $>10^3$. The principle of signal reconstruction using inverse transform with a generalized inverse matrix under the conditions of major over-sampling (>10$^5$) as was reported in Belov, M. E.; Foley, P. *Proceeding of the 52$^{nd}$ ASMS Conference*, Nashville, Tenn., 2004, and successfully implemented in experiments using multiplexed orthogonal TOF, as reported in Kimmel, J. R., Yoon, O. K., Zuleta, I. A., Trap, O.; Zare, R. N. *J. Am. Soc. Mass Spectrom.*, 2005, 17, 1117-1130. In general, given an inverse matrix of N×N elements, S$^{-1}$, and a detected signal vector of M elements, y, where M is a multiple of N and M>>N, the latter is split into N bins to enable deconvolution of the original A-element signal vector, z, in M/N inverse transforms.

$$z = S^{-1} \cdot y$$

The details of the multilayer signal reconstruction where a modulation bin comprises multiple TOF mass spectra that, in turn, encompass a large number of TOF bins are given below. Importantly, the compression of the experimental multiplexed IMS-TOF signal (i.e., removal of zero entries from TOF spectra) yielded a fully reconstructed 2D separation in less than a minute, an attractive feature, for example, for on-line LC fractionation coupled to a multiplexed IMS-TOF MS instrument.

Figure 3:
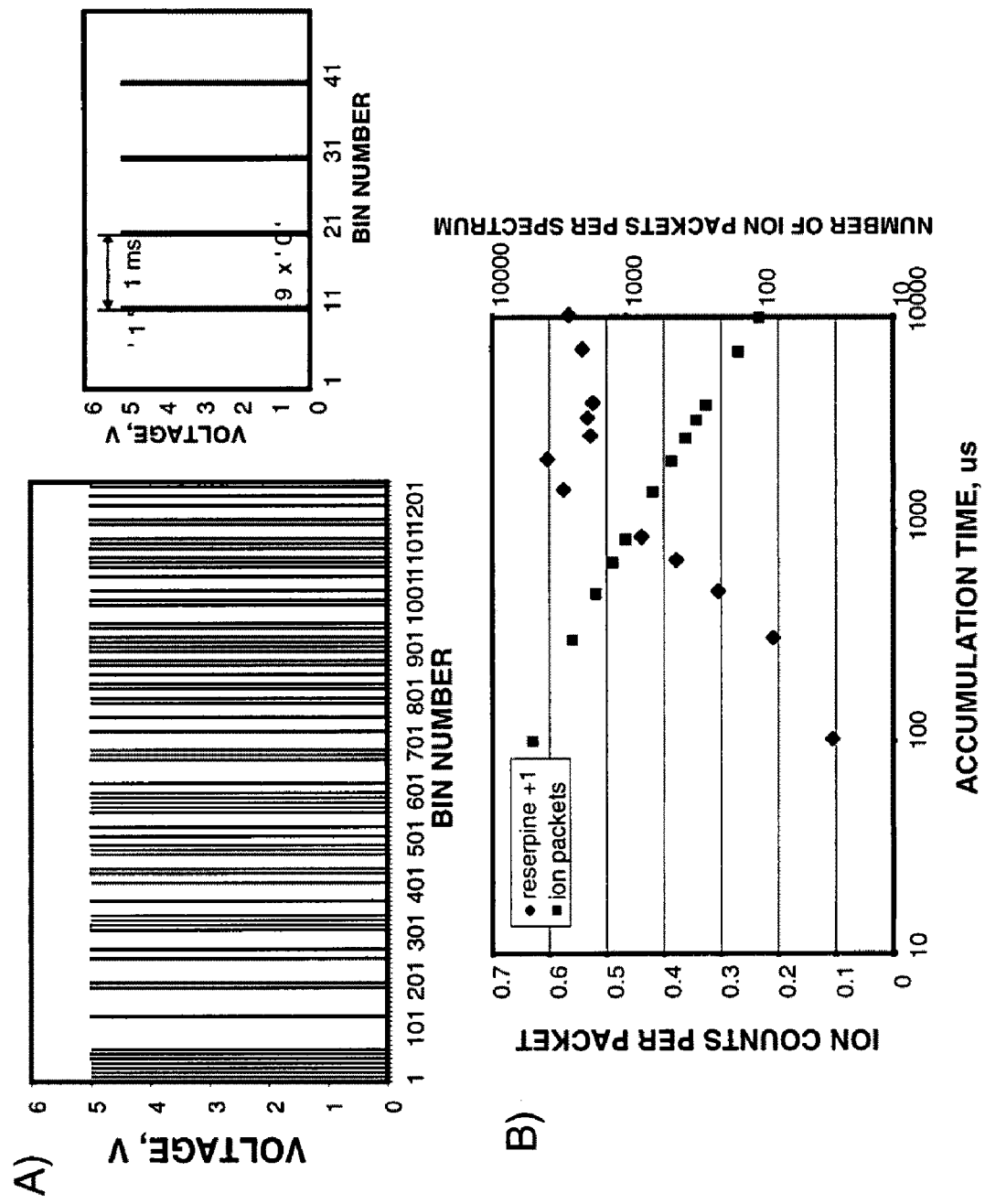
FIG. 3A shows the experimental extended 7-bit maximum length pseudo random sequence used in experiments which demonstrated a preferred embodiment of the present invention. Each pulse corresponds to the ion gating into the IMS drift tube. The inset shows a portion of the sequence. The gating pulse duration was 100 µs. The shortest interval between the gating pulses was 900 µs and the longest was 6900 µs. To perform signal reconstruction, the extended 1270-element sequence was folded into a 127-element weighed vector, with each element obtained by summing 10 preceding elements.
FIG. 3B shows the dependence of the 1 µM reserpine signal per single TOF scan on the ion accumulation time in the hourglass ion funnel. Data were acquired with IMS-TOF (Q-Star Pulsar) MS operated in the signal averaging mode.

A preferred part of signal reconstruction is the ability to perform an inverse transform with a generalized weighed matrix under the conditions of significant over-sampling. An example of such over sampling is represented by the experimental maximum length pseudo random sequence (PRS) shown in FIG. 3A. The total number of modulations bins in the experimental PRS is 127, with each modulation bin incorporating 10 sub-modulation bins. The number of TOF bins in each sub-modulation bin is 62,500. The durations of experimental modulation, sub-modulation and TOF bins are 1 ms, 100 μs, and 1.6 ns, respectively. An extended 127-ms-long PRS incorporates 1270 elements (i.e., the number of sub-modulation bins in the sequence, 127×10=1270). In these experiments, adjacent 100-μs long gate pulses (i.e., digital '1's in the extended sequence) are separated by "accumulation" sub-modulation bins (i.e., digital '0's) to enable ion accumulation between ion releases into the IMS drift tube, minimize ion cloud overlap due to thermal diffusion and maintain short fixed gate opening time. To perform signal reconstruction, the extended PRS was folded into a weighed PRS, such that the number of consecutive "accumulation" sub-modulation bins constitutes the sequence weight.

$$\text{PRS\_weighed}_i = \sum_{j=0}^{M} \text{PRS\_extended\_zeros}_{ij}$$

where i the modulation bin number, j is the sub-modulation bin number, M is the number of sub-modulation bins within a modulation bin, PRS_extended_zeros$_{ij}$ is the counter that corresponds to the number of digital '0's in the extended PRS sequence, and PRS_weighed$_i$ is the element of the folded weighed PRS.

For instance, if two adjacent '1's in the extended sequence are separated by 9 consecutive '0's, the modulation bin would then be represented in the folded sequence with a weight of 9. If all sub-modulation bins within a particular modulation bin were '0's, the weighed element in the folded sequence would be 0. Weighing approach could also be described by generation of a 7-bit maximum length PRS using a shift register approach. The sequence would be then stretched, so that each '1' would become a series of '0000000001', while each '0' would be represented as '0000000000'. The extended PRS was used for data acquisition and then folded with weights, as described above, to generate an inverse matrix and perform signal reconstruction. Folding, down-shifting and taking a matrix inverse brought about a 127×127 element inverse matrix.

Let one consider an extended PRS that consists of N-modulation bins, each encompassing M sub-modulation bins. Each of these sub-modulations bins, in turn, includes L time-of-flight (TOF) bins. If an inverse matrix S$^{-1}$ is obtained with the weighed PRS, the signal reconstruction would then be performed as follows:

$$z_{njk} = \sum_{j=0}^{N-1} s_{ni}^{-1} y_{ijk} \qquad (14)$$

where n is the row index of the inverse matrix, n∈[0, N−1], i is the column index of the inverse matrix, i∈[0, N−1], j is the sub-modulation bin number, j∈[0 μM−1], and k is the TOF bin number, k∈[0, L−1], s$_{ni}$ is the inverse matrix element, y$_{ijk}$ and z$_{njk}$ are the detected and reconstructed signals, respectively, corresponding to a single TOF bin. Importantly, to enable inverse transform, the number of rows and columns of the inverse matrix must be equal to the number of modulation bins. Following Equation 14, signal reconstruction is performed independently for each sub-modulation bin, and the total of M transforms is needed to complete the algorithm. It's noteworthy that no averaging or/and summing is performed to obtain the original data vector with the inverse transform of the generalized weighed matrix S$^{-1}$ and reconstruction resolution is equal to a TOF bin width.

Figure 2:
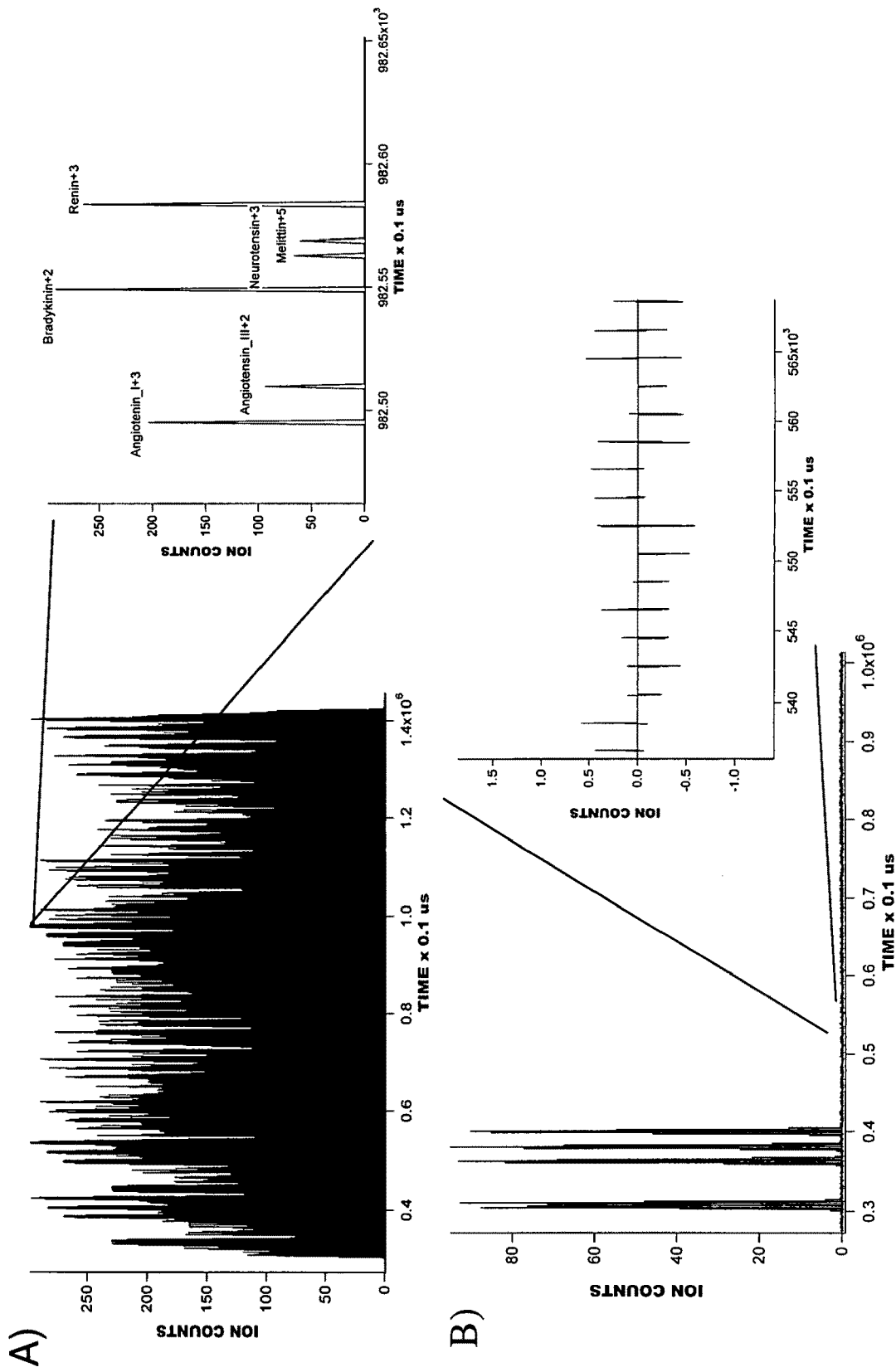
FIG. 2A shows the modeled multiplexed IMS-TOF MS raw data signal obtained with an equimolar mixture of angiotensin_I+3 (m/z 432.89), angiotensin_III+2 (m/z 459.25), bradykinin+2 (m/z 530.78), neurotensin+3 (m/z 558.314), N-acetylrenin+3 (m/z 600.994), melittin+5 (m/z 570.15) in experiments which demonstrated a preferred embodiment of the present invention. One hundred ions of each peptide were introduced into the modeled IMS drift tube during PRS gating pulses.
FIG. 2B shows the reconstructed modeled multiplexed IMS-TOF spectrum of the equimolar mixture of peptides used in FIG. 2A in experiments which demonstrated a preferred embodiment of the present invention. Reconstruction was performed at a resolution of 100 ns.

FIG. 2A shows the modeled raw signal obtained with an equimolar mixture of six peptides. To generate this signal, 100 ions for each peptide were introduced into the IMS drift tube during each 200 us-long "gate open" event in a 9-bit modulation sequence. The modeling assumed ideal ion transmission; i.e. all ions gated into the IMS region reach the MS detector. A significant intermingling of ion packets is observed in the IMS drift tube. An inset to FIG. 2A shows the MS signal from a portion of the IMS separation corresponding to one TOF mass spectrum. FIG. 2B shows an IMS-TOF MS signal reconstructed by inverse transformation of a 511×511 simplex matrix. A characteristic feature of this reconstruction is the mathematical pseudo-noise observed at the background level, as shown in the inset. Similar background noise has been observed in HT-TOF MS measurements, and Poissonian statistics for the arrival times of ions at the detector have been employed to estimate the magnitude of the baseline noise as a function of mass spectral features and acquisition conditions, as described in Kimmel, J. R., Yoon, O. K., Zuleta, I. A., Trap, O.; Zare, R. N. *J. Am. Soc. Mass Spectrom.*, 2005, 17, 1117-1130. The magnitude of the pseudo-noise was found to be dependent on the temporal separation between two adjacent packets and represents the overlapping of spatial distributions of ion packets launched in different modulation bins. In an extreme case, ion packet broadening due to thermal diffusion results in a significant increase in the pseudo-noise, making multiplexing impractical. Therefore, thermal diffusion imposes a fundamental limitation on the encoding sequence length (i.e., the number of bins in a sequence), and sets the minimum interval desirable between two adjacent gate pulses. On the other hand, the sequence length must not exceed the time scale of an IMS separation in the standard averaging mode, as no SNR improvement can be gained on the timescale longer than that of a single signal averaging experiment. To better understand the last statement, one can compare signal averaging against multiplexing, where two acquisitions in the multiplexed mode are performed on a timescale of one acquisition in signal averaging mode. The SNR improvement obtained using the multiplexed approach is $\sqrt{2}$ compared to signal averaging; four acquisitions in the multiplexed mode provide a factor of 2 gain, while signal averaging would result in $\sqrt{2}$ gain. The obtainable gain thus depends on the number of multiplexed acquisitions made on the timescale of a single signal averaging experiment; the advantage of multiplexing is that one can perform multiple acquisitions in the multiplexed mode on the timescale of the signal averaging experiment. In the above example, the signal averaging approach would provide the same SNR if performed on a time scale two times longer than that of the multiplexed experiment. Multiplexing provides the basis (due to the encoding-decoding algorithm) for more acquisitions on the timescale of a single signal averaging experiment, and the benefits of multiplexing would only be realized for a portion of the encoding sequence that corresponds to the duration of the IMS separation in signal averaging mode.

The experimental implementation of multiplexed IMS-TOF measurements was guided by these modeling results and using similar signal reconstruction routines. FIG. 3A shows the encoding sequence used for the multiplexed IMS-TOF MS experiments. The important difference between this sequence and the conventional encoding sequences used in HT photospectrometry, described in Harwit, M.; Sloane, N. J. *Hadamard Transform Optics*; Academic Press: New York, 1979; HT-TOF MS, described in Brock, A.; Rodriguez, N.; Zare, R. N. *Anal. Chem.*, 1998, 70, 3735-3741; HT-CE, described in Kaneta, T.; Yamaguchi, Y.; Imasaka, T. *Anal. Chem.*, 1999, 71, 5444-5446 and HT-IMS, described in Clowers, B. H.; Siems, W. F.; Hill, H. H.; Massick, S. M. *Anal.Chem.*, 2006, 78, 44-51 is that the adjacent digital '1' events (i.e., "gate open" events) in the sequence of these experiments are separated by '0' events (i.e., "gate closed" events), while a typical encoding sequence in HT experiments has combinations of consecutive '1' events.

Three objectives were achieved by introducing delays between two adjacent ion releases into the IMS drift tube. First, extending the timing interval between two neighboring ion packets reduced the detrimental effects of diffusion-driven ion dispersion upon signal reconstruction, thus decreasing the mathematical noise upon signal reconstruction. Second, the constant short gate opening time (~100 μs, see inset) minimized peak broadening due to the gating term, $t_g$, in Equation 3. For comparison, in an HT-IMS experiment with a conventional 13-bit PRS implemented at a rate of 150 μs per modulation bin, the longest gate open event would be ~2 ms, as shown in Clowers, B. H.; Siems, W. F.; Hill, H. H.; Massick, S. M. *Anal.Chem.*, 2006, 78, 44-51. As a result, the gate opening time would on average exceed that of the signal averaging mode by ~3-4 fold, resulting in peak broadening. Third, ions delivered to the ion funnel from a continuous source can be more efficiently accumulated between two adjacent releases for the shorter periods without exceeding the level at which space charge effects would be problematic, and resulting in a increase in the charge density per ion cloud released to the IMS drift tube. To perform signal reconstruction, 1270 element modulation sequence was folded into a 127-element vector, such that each vector element was a sum of the 10 preceding elements in the modulation sequence. The weighing algorithm is described in detail above. As a result, a weighed 127-element PRS was obtained to be used for generation of a generalized weighed matrix and inverse transform.

Since both standard and multiplexed modes incorporated ion accumulation between adjacent gate pulses, the ion signal intensity for one TOF mass spectrum was examined. The interval between two adjacent pulses in the experimental PRS (i.e., ion accumulation intervals), shown in FIG. 3A, varied between 1 ms and 7 ms, while IMS in the signal averaging mode was conducted using one ion packet ejected from the ion accumulation trap every 127 ms. FIG. 3B shows the charge density of a trapped ion cloud as a function of the accumulation time in the signal averaging mode. This dependence revealed ion signal saturation from ESI of a 1 μM sample of reserpine for an accumulation time of ~2 ms. Therefore, when comparing the multiplexed versus signal averaging IMS modes of operation, no signal enhancement using the signal averaging IMS mode could be achieved for accumulation events longer than 2 ms with the current design of the ion funnel (presumably due to space charge constraints), and SNR improvement will only be attained via the multiplexing gain or mechanisms other than ion accumulation in the ion funnel trap, e.g., the overlapping of ion packets in the TOF extraction region. FIG. 3B also indicates that only a portion of the multiplexed experiment, corresponding to the accumulation intervals of less than 2 ms, could be performed at a duty cycle of ~95%. Longer accumulation intervals (>2 ms) within the extended PRS exhibited ion losses similar to those experienced in the signal averaging mode.

Figure 4:
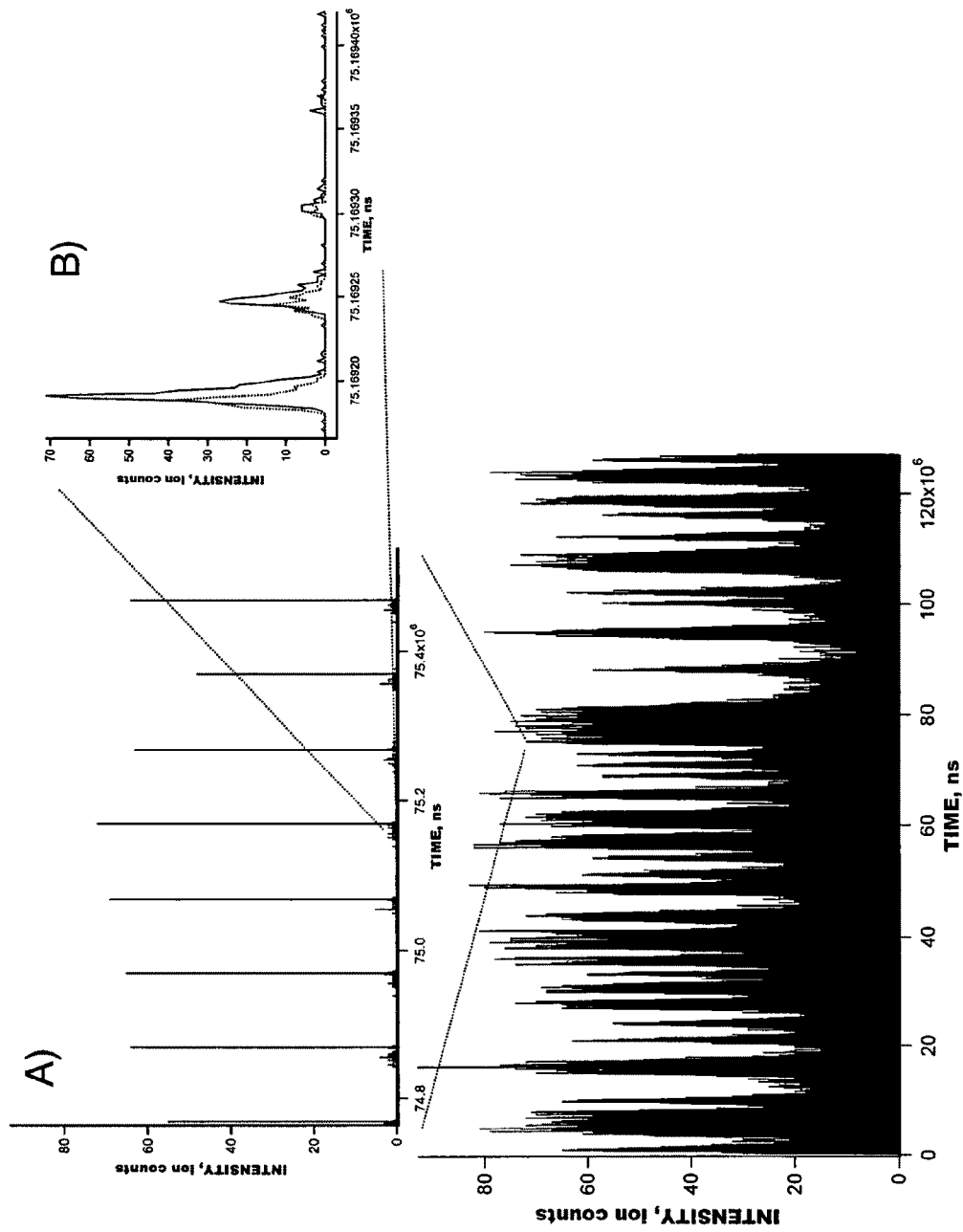
FIG. 4. shows the experimental raw data signal obtained with 1 µM solution of reserpine in a multiplexed IMS-TOF MS (Q-Star Pulsar) experiment which demonstrated a preferred embodiment of the present invention. The multiplexed IMS-TOF raw signal was acquired at 1.6 ns resolution and summed over 1000 IMS acquisitions, corresponding to 127 s. Inset A shows a small portion of the multiplexed IMS-TOF MS measurement corresponding to 8 mass spectra. Inset B shows a portion of one of the mass spectra in Inset B, corresponding to the reserpine peak. The signal maximum obtained in the signal averaging IMS-TOF experiment (dashed line) is compared to the raw (unreconstructed) multiplexed IMS-TOF signal (solid line).
Figure 5:
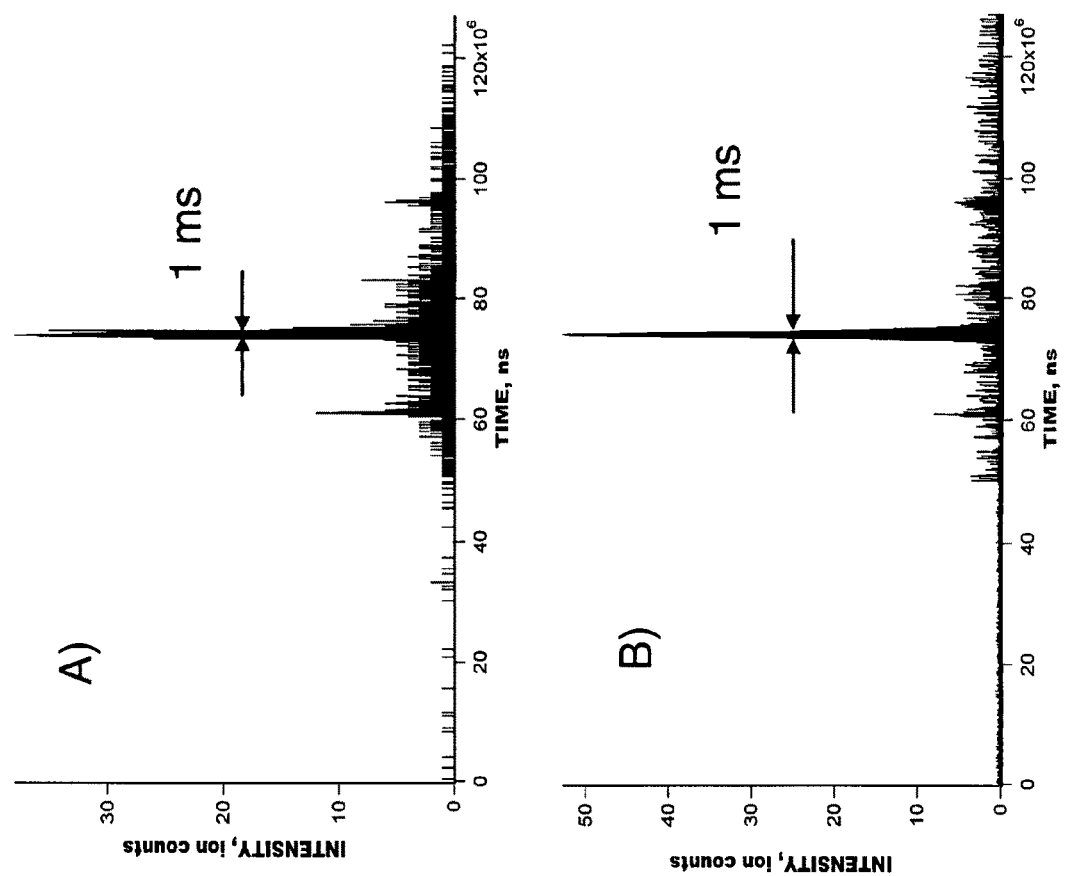
FIG. 5A shows a 1 µM reserpine signal acquired with the IMS-TOF MS (Q-Star MS Pulsar) instrument operated in the signal averaging mode in experiments which demonstrated a preferred embodiment of the present invention. Experimental conditions were identical to that in FIG. 3A.
FIG. 5B shows a reconstructed 1 µM reserpine signal acquired in the multiplexed experiment with the IMS-TOF MS in FIG. 4. Temporal resolution of the reconstructed signal is 1.6 ns. Each IMS separation comprises 1270 TOF scans, and a total of 1000 IMS separations were summed both in the multiplexed and signal averaging modes.
Figure 6:
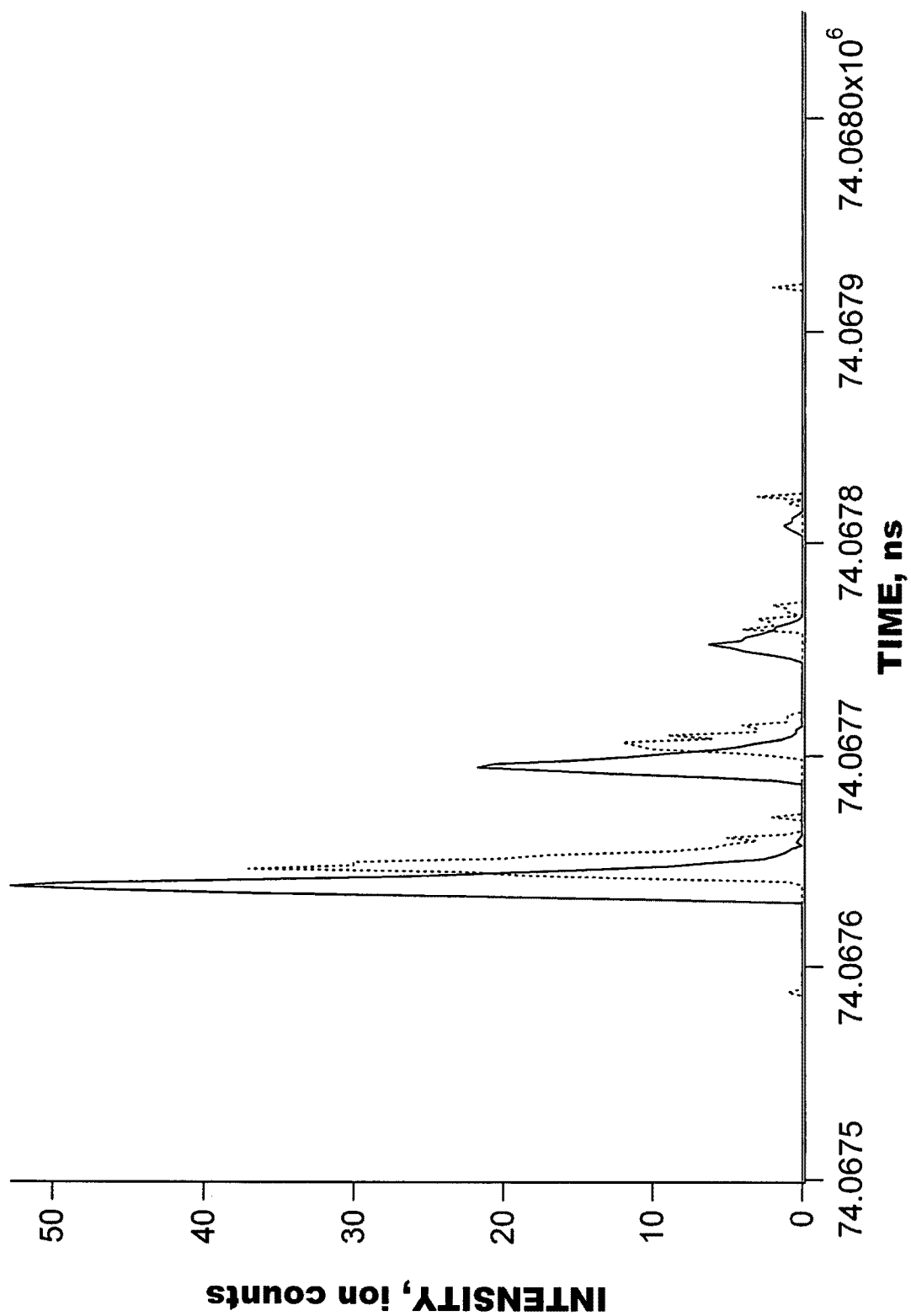
FIG. 6. shows a portion of the reconstructed multiplexed IMS-TOF separation in FIG. 5A (solid line) superimposed with that of IMS-TOF separation conducted in the signal averaging mode in FIG. 5B (dashed line). Noise level in the conventional IMS-TOF separation corresponds to single ion counts.
Figure 7:
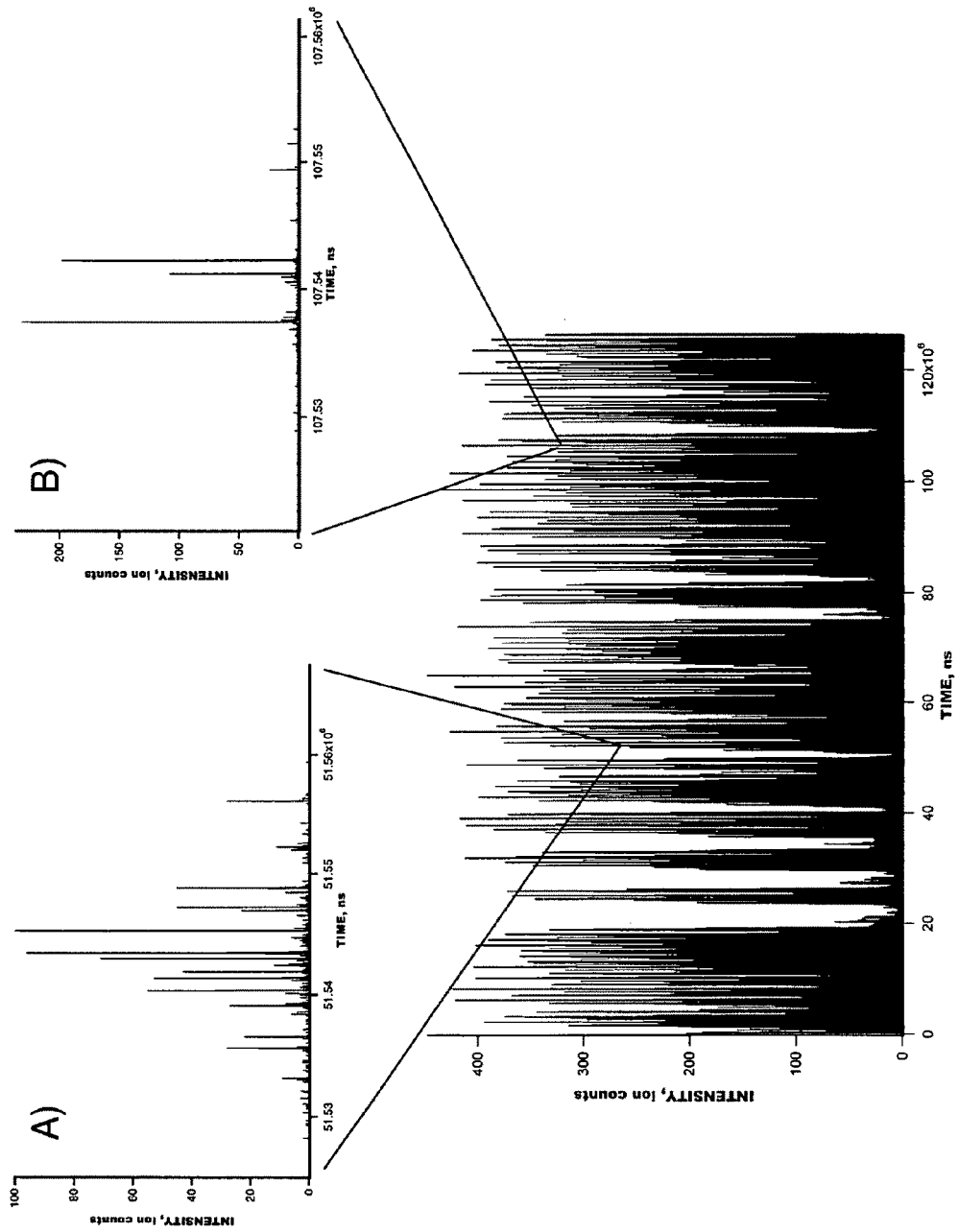
FIG. 7. shows experimental raw data signal acquired in the multiplexed IMS-TOF MS (Agilent) measurement with 1 µM solution of bradykinin, angiotensin I, fibrinopeptide and neurotensin in experiments which demonstrated a preferred embodiment of the present invention. The multiplexed IMS-TOF raw signal was acquired at 1.6 ns resolution and summed over 1000 IMS acquisitions, corresponding to 127 s. Multiplexed IMS separation encompasses 1270 TOF spectra. Insets A and B show small portions of the multiplexed IMS-TOF separation corresponding to single mass spectra.
Figure 8:
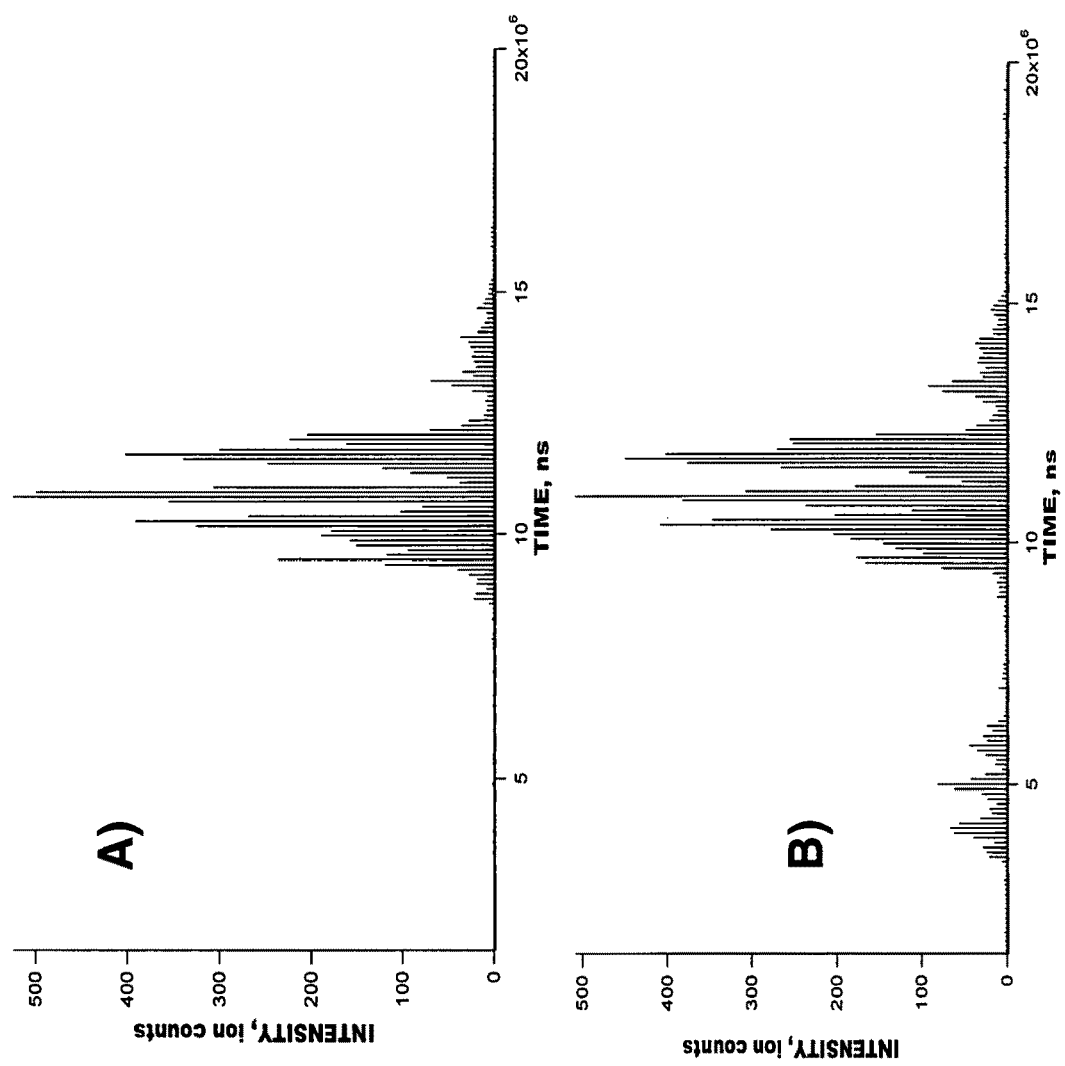
FIG. 8A shows the signal obtained with the peptide mixture in FIG. 7 using IMS-TOF MS (Agilent) instrument operated in the signal averaging mode. The experimental conditions were identical to those used in FIG. 7.
FIG. 8B shows the reconstructed IMS-TOF signal from the multiplexed experiment in FIG. 7. Each IMS separation in FIG. 8A-B comprises 1270 TOF mass spectra, and a total of 100 IMS separations were summed.
Figure 9:
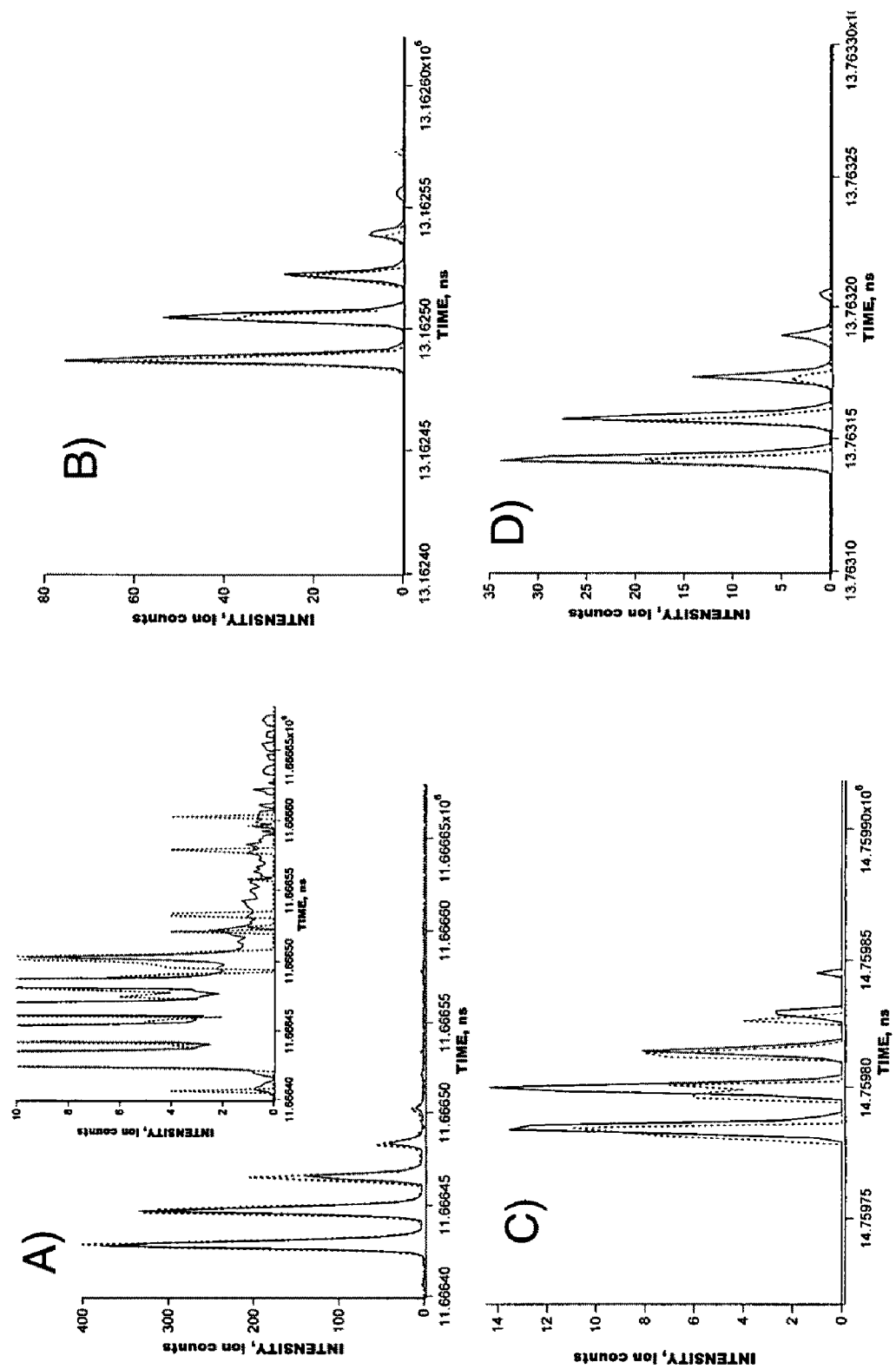
FIG. 9. shows the superimposed portions of the IMS-TOF MS separations performed in the multiplexed (solid line) and signal averaging modes (dashed line) in FIG. 8. The IMS-TOF MS (Agilent) instrument was operated under the conditions described in FIG. 7A. A portion of one out of several TOF mass spectra corresponding to bradykinin signal; the inset shows noise levels for both signal averaging and multiplexed modes; B) angiotensin I signal; C) neurotensin signal, and D) fibrinopeptide signal.

FIG. 4 shows the raw signal obtained with a 1 μM reserpine solution using the IMS-TOF Q-Star Pulsar mass spectrometer in the multiplexed mode. IMS-TOF analysis in FIG. 4 encompasses 1270 concatenated TOF spectra acquired at a resolution of 1.6 ns, each spectrum being a sum of 1000 TOF mass spectra. The total number of ion packets in the IMS drift tube during a single IMS separation was 64 and each IMS separation was conducted in 127 ms. The inset A shows the detected signal during a small portion of the IMS separation corresponding to eight mass spectra. Since ion packets are encoded in one (IMS) dimension of the 2D separation, the other dimension (MS) can be independently analyzed and compared with the signal averaging approach. The inset B shows a portion of one of the mass spectra generated from the raw (unreconstructed) multiplexed signal in FIG. 4 (solid line) in comparison with the maximum observed in a signal averaging IMS-TOF experiment (dashed line). On average, the signal intensity from the raw multiplexed signal was found to exceed the maximum observed in the signal averaging experiment. FIG. 5 shows the comparison between the reconstructed signal acquired in the multiplexed experiment in FIG. 4 and that acquired in the signal averaging mode. The IMS-TOF MS was operated under conditions identical to those in FIG. 4, so that each IMS separation was performed in 127 ms and comprised 1270 TOF mass spectra. Both multiplexed and signal averaging mode separations were acquired over a period of 127 s, corresponding to 1000 IMS acquisitions. Signal reconstruction in FIG. 5B was performed at a resolution of 1.6 ns. The only difference between IMS-TOF separations in FIG. 5A and FIG. 5B was the number of ion packets present in the IMS drift tube at a given time. In the experiment conducted in the signal averaging mode (FIG. 5A), only one ion packet was injected into the drift tube in the course of the entire 127-ms long IMS separation, while, in the multiplexed experiment, 64 ion packets were present in the IMS drift region at the end of each IMS separation. Two-dimensional signal reconstruction enabled the comparison of the multiplexed and signal averaging experiments in both the IMS and MS dimensions. In the IMS dimension, the reconstructed signal was found to match that of the conventional IMS for both the drift time and peak width, implying no detrimental effects on the IMS resolving power due to multiplexing. FIG. 6 shows a small portion of both the multiplexed (reconstructed) and signal averaging IMS-TOF analyses from FIG. 5, representing a small segment of one TOF mass spectrum and showing peaks due to reserpine ions. When compared to the data obtained with the IMS-TOF in signal averaging mode, a ~10-fold SNR increase was observed for the reserpine signal in the multiplexed experiment, exceeding the theoretical multiplexing gain of 5.6 for a sequence of 127 elements. FIG. 7 shows the raw multiplexed data obtained with a 1 µM mixture of bradykinin, angiotensin I, fibrinopeptide and neurotensin in the multiplexed experiments using an IMS-Agilent TOF MS instrument. Since multiple species with different mobilities are gated into the IMS, ions from different ion packets are intermingled in the TOF extraction region, representing a challenge for signal reconstruction. The insets A and B show portions of the IMS separation corresponding to single TOF spectra. Signal acquisition parameters, including TOF scan and IMS separation durations, TOF digitization rate, and the number of IMS acquisitions were the same as for the multiplexed IMS-TOF (Q-Star) MS measurements (see FIG. 5 and FIG. 6). FIG. 8 shows a comparison of data acquired in the multiplexed and signal averaging modes. FIG. 8A demonstrates the IMS-TOF (Agilent) signal acquired in the signal averaging mode, while FIG. 8B shows the reconstructed signal obtained in the multiplexed experiment in FIG. 7. Similar to FIG. 5, both measurements used identical experimental conditions. The TOF spectrum and IMS spectrum acquisition rates were 100 µs and 127 ms, respectively, and each dataset represents a sum of 1000 IMS acquisitions. Signal reconstruction was performed with a single TOF bin resolution of 1.6 ns. A comparison between FIG. 8A and FIG. 8B reveals that the drift times and IMS resolving power (separation peak width) for the reconstructed multiplexed IMS-TOF signal (FIG. 8B) matches that of the signal averaging approach (FIG. 8A). The IMS-TOF signal at drift times of about 5 ms was due chemical noise variation and was not related to signal reconstruction algorithm. A detailed comparison of signal averaging and multiplexed datasets is shown in FIG. 9, where small portions of the TOF mass spectra, corresponding to the detected peptides from both the multiplexed and signal averaging experiments, are superimposed. FIG. 9 is obtained by expanding short separation regions from FIG. 8. Interestingly, reconstructed multiplexed spectra exhibited SNR improvements both for higher (e.g., bradykinin in FIG. 9A) and lower abundance species (e.g., neurotensin in FIG. 9C and fibrinopeptide in FIG. 9D). For the signal averaging mode, the noise level corresponds to 3-4 ion counts, thus a SNR of ~100 is obtained for the bradykinin signal in FIG. 9A (FIG. 9A, dashed line). The corresponding noise level for the multiplexed measurement was ~0.4-0.5 (FIG. 9A, solid line), resulting in ~8-fold greater SNR for the same peptide. The noise levels from both multiplexed and signal averaging experiments are shown in the FIG. 9A inset. An increase in the SNR for lower abundance species (FIG. 9C, FIG. 9D) is evident in the isotopic distributions detected in the multiplexed verses the signal averaging experiments. Data obtained in the signal averaging mode show distorted distribution of isotopic peaks, missing isotopic peaks and noisy line shapes due to limitation in ion statistics.

An important characteristic that distinguishes the current approach from the earlier implementations of the HT-IMS shown in Clowers, B. H.; Siems, W. F.; Hill, H. H.; Massick, S. M. *Anal.Chem.*, 2006, 78, 44-51 and Szumias, A. W.; Ray, S. J.; Hieftje, G. M. *Anal. Chem.*, 2006, 78, 474-4471 is the combination of ion accumulation with multiplexing. In the ideal scenario, the ion trapping efficiency would remain constant for accumulation times extending to >10 ms. Given a 1 ms-long modulation bin comprising 10 sub-modulation bins (as in the current approach) and a gate opening time of 100 µs, an average weighed accumulation time for a 7-bit sequence would be ~2 ms, resulting in a ~20-fold (2 ms/100 us) increase in the ion cloud charge density. Therefore, an expected SNR increase, SNR_mult, would be:

$$\text{SNR\_mult} \approx \text{Efficiency}_{trap} \times \text{Gain}_{mult} \qquad (12)$$
$$= 20 \times 5.6$$
$$\approx 100$$

$$\text{Gain}_{mult} \equiv \frac{\sqrt{2^N - 1}}{2} \qquad (13)$$

where Efficiency$_{trap}$ is the charge density increase due to ion accumulation as compared to that of the continuous beam, Gain$_{mult}$ is the multiplexing gain, and N is the number of PRS bits. If HT-IMS is operated at higher modulation rate based on, for example, a 10-bit sequence, an SNR increase would be limited to a multiplexing gain of ~16. The drawback of running the instrument at higher modulation rate would be an increase in mathematical pseudo noise due to diffusion-driven ion cloud overlap and the loss of multiplexing advantage.

In measurements using a 1 µM solution of reserpine, a charge collector positioned immediately downstream of the hourglass ion funnel gave rise to an ion current of ~50 pA. This current translates to the maximum of ~3×10$^5$ singly charged ions that could be accumulated in the ion funnel trap in 1 ms. FIG. 3B shows that charge density per ion packet does not increase with an increase in ion accumulation times longer than ~2 ms. Therefore, the charge capacity of the ion funnel trap under current experimental conditions was limited to ~10$^6$ ions. Based on the balance of Coulombic repulsion and effective potential forces, the theoretical charge capacity of the present ion funnel trap has been estimated by Tolmachev, A. V.; Udseth, H. R.; Smith, R. D. *Anal.Chem.*, 2000, 72, 972-978 as >10$^7$ elementary charges, exceeding the present experimental situation by more than one order of magnitude. An increase in the ion funnel effective potential due to an increase in the rf frequency and amplitude can potentially bridge this gap between theory and experiment. Based upon Equation 12, the accumulation of greater ion populations (e.g., by extending the linear dynamic range of our ion funnel trap to enable a linear increase in ion populations at accumulation times up to ~10 ms) could potentially result in a further SNR improvement as compared to that experimentally achieved, and an increase in the duty cycle to ~95% for ion utilization.

The experimental observation of an SNR increase greater than the multiplexing gain (see FIG. 6 and FIG. 9) is explained as follows. Since both conventional and multiplexed IMS-TOF measurements were performed using the ion trapping mode, and there was no increase in the ion packet charge density for accumulation times greater than 2 ms (see FIG. 3B), it is inferred that the SNR improvement is due to the multiplexing gain. This would be the case for one-dimensional multiplexed IMS separations, where the experimental gain could never exceed the theoretical multiplexing gain. However, in two-dimensional separations, an overlap of the ion clouds in TOF extraction region due to thermal diffusion (as shown in the raw multiplexed data in FIG. 4B) increases the number of ions to be pulsed to the mass spectrometer in a single scan as compared to that of the standard IMS separation. This is also confirmed in the modeled data (see FIG. 2A), so that peak intensities of ~300 ions were observed with only 100 ions introduced per packet into the IMS drift tube. The inset B in FIG. 4 and comparison of signal intensities in FIG. 4 and FIG. 5A consistently show that even before signal reconstruction ion intensities in the multiplexed IMS-TOF experiment exceed the signal maximum obtained in the signal averaging experiment. In these measurements both the number of TOF packets with ions and the number of ions per TOF packet, are increased, resulting in a SNR increase greater than the multiplexing gain. Thus, a significant part of the multiplexing gain with IMS-TOF measurements arises from a second separation dimension (i.e., the MS). More rigorous validation of the SNR improvement due to ion packet overlap in the TOF extraction region is achievable via reducing the number of bits in the encoding sequence, which would enable further spatial separation of the ion packets.

Finally, a multiplexed IMS-TOF resolution in the IMS dimension (~70 for the IMS-Q-Star and ~45 for the IMS-Agilent TOF MS) was found to be similar to that for the conventional IMS-TOF (see FIG. 5 and FIG. 8), implying a weak dependence of ion drift times on the space charge in the multiplexing experiments. Unlike atmospheric pressure HT-IMS where IMS resolution is primarily dependent on the gate opening time, in a lower pressure (~4 Torr) IMS separation, a separation peak width (~1 ms fwhm for the IMS-QStar TOF MS platform) is primarily determined by thermal diffusion (see Equation 3). Further increases in the pressure and electric field strength are projected to facilitate an increase in the multiplexed IMS resolution, since the thermal diffusion term will be reduced while the gate opening time would remain constant (see FIG. 3).

These experiments thereby demonstrated the multiplexed IMS-TOF MS approach of the present invention, both as modeled and experimentally implemented using an ESI source. Previous results using Hadamard IMS have been limited by diffusion phenomena. Data reconstructed in the multiplexed IMS-TOF MS experiments using the new approach of the present invention, and proper selection of the encoding sequence, showed a ~10-fold increase in SNR can be obtained compared to the same instrument operating in the conventional signal averaging mode for a mixture of peptides. Further sensitivity improvements are attainable by increasing the charge capacity of the ion accumulation trap and the efficiency of ion ejection from the trap with shorter gate pulses. Such an implementation would drastically minimize ion losses in the ESI-IMS interface, potentially providing >95% ion utilization efficiency. Since a multiplexed IMS-TOF MS separation can be obtained on a time scale of ~100 ms, the present invention provides a extremely high-throughput and sensitive platform for applications in proteomics and system biology applications. Integration of the multiplexed IMS-TOF MS platform with on-line RPLC fractionation enables complete sample analysis involving 3D separations having substantially increased throughput compared to LC-MS, making such an approach highly attractive for many clinical applications.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Finally, all publications, patents, and patent applications cited in this specification are herein incorporated by reference to the extent not inconsistent with the present disclosure as if each were specifically and individually indicated to be incorporated by reference and set forth in its entirety herein.

We claim:

1. A method for analyzing analytes from a sample introduced into a Spectrometer comprising the steps of
   a. generating a pseudo random sequence of a modulation bins;
   b. organizing each modulation bin as a series of submodulation bins, thereby forming an extended pseudo random sequence of submodulation bins wherein each submodulation bin is either a gate open event, where analyte is being introduced into the spectrometer, or a gate closed event, where analyte is not being introduced into the spectrometer, the submodulation bins are of equal duration, and each modulation bin consists of either a gate open event followed by a series of gate closed events, or consists a series of gate closed events;
   c. releasing the analytes in a series of analyte packets into a Spectrometer with a series of gate open events according to the pseudo random sequence of modulation bins wherein each ion packet consists of ions released by a given gate open event, thereby generating an unknown original ion signal vector;
   d. detecting the analytes at a detector, wherein analytes of sequential packets are intermingled at the detector thereby generating a plurality of analyte signal subvectors equal to the number of submodulation bins;
   e. characterizing the sample using the plurality of analyte signal subvectors.

2. A method for analyzing an ion beam from a sample introduced into an Ion Mobility Spectrometer comprising the steps of
   a. accumulating ions from the sample in an ion trap having a gate;
   b. generating a pseudo random sequence of a modulation bins;
   c. organizing each modulation bin as a series of submodulation bins, thereby forming an extended pseudo random sequence of submodulation bins wherein each submodulation bin is either a gate open event or a gate closed event, the submodulation bins are of equal duration, and each modulation bin consists of either a gate open event followed by a series of gate closed events, or a series of gate closed events;

d. releasing the ions in a series of ion packets with a series of gate open events according to the pseudo random sequence of modulation bins wherein each ion packet consists of ions released by a given gate open event, thereby generating an unknown original ion signal vector;

e. accelerating the accumulated ions of each ion packet released from the ion trap through an Ion Mobility Spectrometer;

f. detecting the accelerated ions at a detector, wherein ions of sequential packets are intermingled at the detector thereby generating a plurality of ion signal subvectors equal to the number of submodulation bins;

g. characterizing the sample using the plurality of ion signal subvectors.

3. The method of claim 1, wherein the characterizing step comprises the steps of folding the extended pseudo random sequence of submodulation bins to produce weighed pseudo random sequence wherein the weights account for the accumulation time before each gate open event, generating a weighed matrix from the weighed sequence using a shift register technique, generating an inverse weighed matrix, reconstructing the unknown original ion signal vector by multiplying the inverse matrix by each of the ion signal subvectors and organizing the products into a vector.

4. A method for analyzing an ion beam from a sample introduced into an Ion Mobility Spectrometer interfaced with a Time of Flight Mass Spectrometer comprising the steps of:

a. accumulating ions from the sample in an ion trap having a gate;

b. generating a pseudo random sequence of a modulation bins;

c. organizing each modulation bin as a series of submodulation bins, thereby forming an extended pseudo random sequence of submodulation bins wherein each submodulation bin is either a gate open event or a gate closed event, the submodulation bins are of equal duration, and each modulation bin consists of either a gate open event followed by a series of gate closed events, or a series of gate closed events;

d. releasing the ions in a series of ion packets with a series of gate open events according to the pseudo random sequence of modulation bins wherein each ion packet consists of ions released by a given gate open event, thereby generating an unknown original ion signal vector;

e. accelerating the accumulated ions of each ion packet released from the ion trap through an Ion Mobility Spectrometer, thereby intermingling the ions from successive ion packets;

f. accelerating the ion packets from the Ion Mobility Spectrometer through a time of flight mass spectrometer;

g. detecting the accelerated ions from the time of flight mass spectrometer at a detector in a series of time of flight bins, wherein ions of sequential packets are intermingled at the detector thereby generating a plurality of ion signal subvectors equal to the number of time of flight bins in each submodulation bin;

h. characterizing the sample using the plurality of ion signal subvectors.

5. The method of claim 3, wherein the characterizing step comprises the steps of folding the extended pseudo random sequence of submodulation bins to produce weighed pseudo random sequence wherein the weights account for the accumulation time before each gate open event, generating a weighed matrix from the weighed sequence using a shift register technique, generating an inverse weighed matrix, reconstructing the unknown original ion signal vector by multiplying the inverse matrix by each of the ion signal subvectors and organizing the products into a vector.

6. The method of claim 1 or 3, further comprising repeating the accumulating, accelerating, and detecting steps for a plurality of sequences, wherein the accelerated ions travel along a flight path such that flight times of the ions to the detector vary with characteristics of the ions, and wherein the characterizing step comprises recovering a mass spectrum of at least one sequence from the intermingled ions.

7. The method of claim 5, wherein each sequence defines a scan, and wherein the characterizing step further comprises summing a plurality of scans.

* * * * *

UNITED STATES PATENT AND TRADEMARK OFFICE
CERTIFICATE OF CORRECTION

PATENT NO. : 7,541,576 B2
APPLICATION NO. : 11/701752
DATED : June 2, 2009
INVENTOR(S) : M E Belov and R D Smith It is certified that error appears in the above-identified patent and that said Letters Patent is hereby corrected as shown below:

Please correct paragraph 0001 of the application and Column 1, lines 6 through 9 of the issued patent as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Eleventh Day of September, 2012

David J. Kappos
*Director of the United States Patent and Trademark Office*